(12) United States Patent
Simon

(10) Patent No.: US 6,284,718 B1
(45) Date of Patent: Sep. 4, 2001

(54) COMPOSITION FOR TOPICAL USE CONTAINING AN ACETYLENIC DIOL, AND USE THEREOF FOR CLEANSING OR REMOVING MAKE-UP FROM THE SKIN, MUCOUS MEMBRANES AND THE HAIR

(75) Inventor: Pascal Simon, Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/497,217

(22) Filed: Feb. 3, 2000

(30) Foreign Application Priority Data

Feb. 12, 1999 (FR) .................................................. 99 01735

(51) Int. Cl.⁷ ....................................................... C11D 1/72
(52) U.S. Cl. .......................... 510/136; 510/119; 510/130; 510/137; 510/158; 510/421
(58) Field of Search .................................... 510/119, 130, 510/136, 137, 158, 421

(56) References Cited

U.S. PATENT DOCUMENTS 3,268,593 * 8/1966 Carpenter et al. .................... 260/615
5,767,054    6/1998 Sprugel et al. .

FOREIGN PATENT DOCUMENTS 0 531 269 A2   3/1993 (EP) .
   893431  *  4/1962 (GB) .

* cited by examiner

*Primary Examiner*—Yogendra N. Gupta
*Assistant Examiner*—Charles Boyer
(74) *Attorney, Agent, or Firm*—Oblon, Spivak, McClelland, Maier & Neustadt, P.C.

(57) ABSTRACT

Compositions suitable for cosmetic and/or dermatological use which contain a oxyethylenated acetylenic diol, and at least one amphiphillic compound having an HLB greater than or equal to 15, in a physiological acceptable medium.

15 Claims, No Drawings

COMPOSITION FOR TOPICAL USE CONTAINING AN ACETYLENIC DIOL, AND USE THEREOF FOR CLEANSING OR REMOVING MAKE-UP FROM THE SKIN, MUCOUS MEMBRANES AND THE HAIR

BACKGROUND OF THE INVENTION

1. Field of the Invention

The invention relates to a composition for topical use, containing an oxyethylenated acetylenic diol, and to its cosmetic use. Furthermore, the invention relates to removing make-up from and/or cleansing the skin, the hair and/or mucous membranes.

2. Discussion of the Background

A make-up-removing composition is expected to be able to remove all kinds of make-up products, e.g., lipstick, powder, eye shadow, foundation, etc., without damaging the skin, and leaving the skin clean and soft. Many make-up-removing products have aqueous bases, e.g., aqueous, aqueous-alcoholic, aqueous-glycolic lotions, and transparent aqueous gels. The products contain dissolved surfactants that facilitate make-up removal by placing the make-up products in suspension. These surfactants should have good make-up removing efficacy, good skin tolerability, and they should provide good stability to the composition containing them.

A surfactant which is effective for cleansing or removing make-up, such as a anionic surfactant, is usually tolerated poorly by the skin. In contrast, a mild surfactant, such as a nonionic surfactant, often has an insufficient detergent activity. Regarding the nonionic surfactants, better make-up-removing efficacy can be obtained by increasing the amount of the surfactant in the composition. However, increasing the amount of the surfactant may lead to stability problems, e.g., recrystallization, coloration, and poor fastness with respect to light and temperature.

Therefore, a need remains for a relatively non-irritant and nonionic surfactant that has good make-up-removing properties at low concentrations.

The document U.S. Pat. No. 3,268,593 describes the use of oxyethylenated acetylenic diols as surfactants and detergents. However, the quantity of these diols that are required to be effective is unsatisfactorily high and thus can lead to poor tolerability by the skin.

SUMMARY OF THE INVENTION

It has now been discovered that among the oxyethylenated acetylenic diols, those having a small number of oxyethylenated groups were the most efficient, even in a low amount, for removing make-up and/or for cleansing the skin, mucous membranes and/or the hair. However, these weakly oxyethylenated diols are difficult to incorporate in topical compositions because they have a low water solubility. The present inventors have discovered that by combining the diols with a amphiphilic compound having an hydrophillic-lipophillic balance (HLB) greater than or equal to 15, it was possible to incorporate the oxyethylenated acetylenic diols easily in a topical composition.

An object of the invention is thus a composition for topical use, containing, in a physiologically acceptable medium, from 0.01 to 0.5% by weight relative to the total weight of the composition, of one or more oxyethylenated acetylenic diol of formula (I):

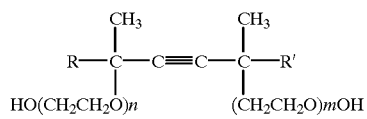

in which:

R and R' represent, independently of each other, an alkyl radical containing from 1 to 10 carbon atoms;

n and m represent a number ranging from 0 to 10, and the sum n+m is from 2 to 10, and at least one amphiphilic compound for dissolving the oxyethylenated acetylenic diol having an HLB of greater than or equal to 15.

The compounds of formula (I) make it possible to obtain compositions which have lasting stability and which are very well tolerated, in particular on account of the efficacy of these compounds at low percentages. In addition, these compounds possess good make-up-removing and cleansing efficacy at low percentages.

Another object of the invention is the cosmetic use of the composition as defined above for cleansing and/or removing make-up from the skin, mucous membranes (lips), the hair and/or the eyes.

Another object of the invention is a cosmetic process for cleansing and/or removing make-up from the skin, mucous membranes, the hair and/or the eyes, characterized in that a composition as defined above is applied to the skin, mucous membranes, the hair and/or the eyes.

DETAILED DESCRIPTION OF THE INVENTION

In formula (I), the radicals R or R' can represent, for example, an ethyl, methyl, propyl, isopropyl, butyl and/or an isobutyl radical. According to one preferred embodiment of the invention, R and R' are identical.

In the compound of formula (I), n and m can be integers or non-integers.

According to one preferred embodiment of the invention, the diol of formula (I) is chosen from oxyethylenated derivatives of 2,4,7,9-tetramethyl-5-decyne-4,7-diol (formula (I) with R=R'=isopropyl), sold by the company Air Products under the name Surfynol, and more especially 2,4,7,9-tetramethyl-5-decyne-4,7-diol oxyethylenated with 3.5 mol of ethylene oxide, sold under the name Surfynol 440.

The amount of oxyethylenated acetylenic diol in the composition of the invention preferably ranges from 0.01 to 0.5% and preferably from 0.05 to 0.5% by weight relative to the total weight of the composition. These ranges include all specific values and subranges there between, including 0.1, 0.15, 0.2, 0.25, 0.3, 0.35, 0.4, and 0.45% by weight.

The amphiphilic compound dissolving the oxyethylenated acetylenic diol can be chosen in particular from compounds which have a solubility in water to at least 5% by weight. Such a compound has an HLB of greater than or equal to 15 and can be ionic, nonionic or amphoteric. It is preferably a nonionic compound.

Nonionic amphiphilic compounds which can be used in the composition of the invention are, for example, alkoxylated or glycerolated alkenyl succinates, such as hexadecenyl succinate 18 EO sold by the company ICI under the name Arlatone 8016, and polyglycerol dodecenyl succinate 3 EO sold by the company BASF under the name Cremophor COS; block copolymers of ethylene oxide and of propylene oxide, such as the Poloxamer products; fatty alkyl ethers of a sugar, such as allylpolyglucosides; sorbitan fatty esters and oxyethylenated sorbitan fatty esters, such as sorbitan laurate 20 EO (Polysorbate 20); oxyethylenated glycerol esters such as the triester of acetic acid and glycereth-7 (glycereth-7 triacetate), and mixtures thereof.

The amount of solubilizing amphiphilic compound can vary within a wide range depending on the amount of acetylenic diol present in the composition and can range, for example, from 0.001 to 10% and preferably from 0.01 to 5% by weight relative to the total weight of the composition. These ranges include all specific values and subranges there between including 0.005, 0.015, 0.025, 0.075, 0.1, 0.5, 0.75, 1, 3, and 4.5% by weight. According to one preferred embodiment of the invention, the weight ratio between the oxyethylenated acetylenic diol and the solubilizing amphiphilic compound preferably ranges from 1:10 to 10:1 and preferably from 1:2 to 2:1. The composition of the invention intended for topical application contains a physiologically acceptable medium, i.e. a medium which is compatible with the skin, including the scalp, mucous membranes and/or the eyes and can constitute in particular a cosmetic and/or dermatological composition.

The composition can be in any pharmaceutical form normally used in cosmetics and dermatology. In particular, the composition may be in the form of an optionally gelled aqueous solution; a dispersion, such as a lotion which is optionally a two-phase lotion; an emulsion obtained by dispersing a fatty phase in an aqueous phase (O/W), (W/O), a triple emulsion (W/O/W or O/W/O), or a vesicular dispersion of ionic and/or nonionic type. The present composition is prepared using procedures well-known to those of ordinary skill in the art.

The composition of the invention can contain, for example, a lotion, a gel, a milk, a make-up-removing lotion or milk, a cleansing lotion or milk, a shampoo, or a shower gel.

The composition according to the invention can comprise a fatty phase based on animal, plant, mineral, silicone, fluoro and/or synthetic oil. The fatty phase can also contain any other fatty substance liable to be present in the fatty phase, such as, for example, fatty acids, fatty alcohols and waxes such as beeswax.

Components of the fatty phase may be, for example, liquid paraffin, liquid petroleum jelly, perhydrosqualene, plant oils (sweet almond oil, palm oil, castor oil, avocado oil or jojoba oil), silicone oils such as polydimethylsiloxanes, which may be phenylated, such as phenyltrimethicones, and volatile silicone oils such as cyclomethicones. Oils and other fatty substances which may be used in the present composition are disclosed in Kirk-Othmer, Encyclopedia of Chemical Technology, Volume 7, Fourth Edition, 1993, pages 572–619, incorporated herein by reference.

The fatty phase can also comprise a make-up-removing oil such as a fatty acid ester, in particular the esters obtained from an alcohol with a straight or branched chain containing from 1 to 17 carbon atoms and from a fatty acid with a straight or branched chain containing from 3 to 18 carbon atoms. The ester can be chosen in particular from the group consisting of dioctyl adipate, octyl (or 2-ethylhexyl) palmitate, diisopropyl adipate, octyl hexanoate, ethyl laurate, methyl myristate, octyldodecyl octanoate, isodecyl neopentanoate, ethyl myristate, myristyl propionate, octyl 2-ethylhexanoate, octyl octanoate, octyl caprate/caprylate, methyl palmitate, butyl myristate, isobutyl myristate, ethyl palmitate, isohexyl laurate, hexyl laurate, isopropyl isostearate and isononyl isononanoate.

The fatty phase can be present in an amount ranging, for example, from 1 to 95% and preferably from 5 to 30% by weight relative to the total weight of the composition in the case of an emulsion. These ranges include all values and subranges there between including 2, 3, 4, 7.5, 10, 15, 20, 25, 35, 45, 55, 60, 75, 80, 85 and 90% by weight.

The composition according to the invention can also comprise an agent for suspending the fatty phase, for example, a copolymer of $C_{10}$–$C_{30}$ alkyl acrylates, a copolymer of acrylic or methacrylic acid, a copolymer of an ester thereof (Pemulen TR1, Pemulen TR2 or Carbopol 1342 from the company Goodrich), or an acrylamide/methylpropanesulphonic acid copolymer (Sepigel from the company Seppic). The present composition may also contain an agent for dispersing the fatty phase, such as an emulsifying or vesicular system based on vesicles, optionally of nanometric size, consisting of ionic lipids (liposomes) or nonionic lipids. Other emulsifiers that may be used in the present composition are disclosed in Kirk-Othmer, Encyclopedia of Chemical Technology, Volume 7, Fourth Edition, 1993, pages 572–619, incorporated herein by reference.

The composition of the invention can also comprise an agent for modifying its viscosity, and can produce textures that are gelled to a greater or lesser extent. Examples of such agents arecellulosic derivatives (carboxymethylcellulose, hydroxyethylcellulose, hydroxypropylmethylcellulose); natural gums such as xanthan gum, guar gum and carob gum, and carrageenans; polycarboxyvinyl derivatives of the Carbomer type (sold by the company Goodrich under the names Carbopol 940, 951 and 980, or by the company 3V-Sigma under the name Synthalen K or Synthalen L).

The composition of the invention can also comprise adjuvants commonly used in the cosmetic, pharmaceutical, and/or dermatological fields. Preferable adjuvants are preserving agents, antioxidants, fragrances, fillers, pigments, UV screening agents, sequestering agents (EDTA), essential oils, dyestuffs, solvents (for instance lower alcohols containing from 1 to 4 carbon atoms, such as ethanol), hydrophilic or lipophilic active agents such as moisturizers, in particular polyols (glycerol, butylene glycol or hexylene glycol), and vitamins and derivatives thereof. Other examples of adjuvants are disclosed in Kirk-Othmer, Encyclopedia of Chemical Technology, Volume 7, Fourth Edition, 1993, pages 572–619, incorporated herein by reference.

Needless to say, a person skilled in the art will take care to select this or these optional additional compound(s) and/or the amount thereof such that the advantageous properties of the composition according to the invention are not, or are not substantially, adversely affected by the addition envisaged.

The composition preferably has a pH which is suitable for application to the skin, generally between 5 and 8, and preferably a pH of from 5.5 to 7.5. These ranges include all values and subranges there between including 5.25, 5.75, 6.0, 6.25, 6.5, 6.75, 7.0 and 7.25.

The composition of the invention is particularly effective for cleansing and/or removing make-up from the skin; mucous membranes, e.g., lip;, superficial body growths such as the hair, and/or the eyes. Moreover, the composition has the advantage of not causing irritation. In particular, the composition may contain a cleansing and/or make-up-removing milk or lotion for the eyes, the lips and/or the skin, in particular facial skin, a shampoo and/or a shower gel.

Having generally described this invention, a further understanding can be obtained by reference to certain spe-

EXAMPLES

Example 1: Lotion

| | |
|---|---|
| 2,4,7,9-Tetramethyl-5-decyne-4,7-diol oxyethylenated with 3.5 mol of ethylene oxide (Surfynol 440) | 0.1% |
| Hexadecenyl succinate 18 EO (Arlatone 8016) | 0.1% |
| Hexylene glycol | 1% |
| EDTA | 0.1% |
| Preserving agents | 0.3% |
| Water | qs 100% |

The constituents are dissolved one by one in water at a temperature of about 75 to 80° C. The solution is left to cool with gentle stirring and water is added to 100%.

The lotion that is obtained is pleasant to use and has very good make-up-removing properties without attacking or irritating the skin, and leaves the skin remaining soft.

Comparative Example 1: Lotion

| | |
|---|---|
| Sodium laureth sulphate/magnesium laureth sulphate/ sodium laureth-8 sulphate/ magnesium laureth-8 sulphate (Empicol BSD 52 FL2 containing 26% active material, sold by the company Albright & Wilson) | 1% |
| Disodium cocamphodiacetate (Miranol C2M containing 38% active material, sold by the company Rhodia Chimie | 1.1% |
| Hexylene glycol | 1% |
| EDTA | 0.1% |
| Preserving agents | 0.3% |
| Water | qs 100% |

The lotions of Example 1 and of Comparative Example 1 were tested in terms of removal of make-up from the eyes, on a panel of 10 individuals. Although it contains much less surfactant, the lotion of Example 1 according to the invention was found to have an identical make-up-removing power to that of the lotion of the comparative example. In addition, the lotion of Example 1 is much more pleasant to use than that of Comparative Example 1 since it does not form a foam, does not leave a sticky film on the eyelids and the eyelashes, and does not irritate the eyes.

Example 2: Make-up-removing Gel

| | |
|---|---|
| 2,4,7,9-Tetramethyl-5-decyne-4,7-diol oxyethylenated with 3.5 mol of ethylene oxide (Surfynol 440) | 0.2% |
| Poloxamer 188 (Lutrol F68 sold by the company BASF) | 0.1% |
| Acrylates/C10–30 alkyl crosspolymer (Pemulen TR2 sold by the company Goodrich) | 0.25% |
| Sodium hydroxide | 0.01% |
| Preserving agent | 0.1% |
| Water | qs 100% |

The constituents are dissolved one by one in water at a temperature of about 75 to 80° C., adding the Pemulen TR2 and sodium hydroxide last. The solution is left to cool with gentle stirring and water is added to 100%.

Example 3: Make-up-removing Milk

| | |
|---|---|
| 2,4,7,9-Tetramethyl-5-decyne-4,7-diol oxyethylenated with 3.5 mol of ethylene oxide (Surfynol 440) | 0.2% |
| Polysorbate 20 | 0.1% |
| Acrylates/C10–30 alkyl crosspolymer (Pemulen TR2 sold by the company Goodrich) | 0.25% |
| Sodium hydroxide | 0.05% |
| Octyl palmitate | 10% |
| Preserving agent | 0.1% |
| Water | qs 100% |

The aqueous constituents are dissolved one by one in the water at a temperature of about 75 to 80° C., adding the Pemulen TR2 and sodium hydroxide last. The oil is then added and is emulsified in the aqueous mixture. The emulsion is left to cool with gentle stirring and is then made up with water in a quantity sufficient for 100%.

The make-up removing milk that is obtained is good for removal of make-up from eyelashes coated with waterproof or non-waterproof mascaras.

Obviously, numerous modifications and variations on the present invention are possible in light of the above teachings. It is therefore to be understood that within the scope of the appended claims, the invention may be practiced otherwise than as specifically described herein.

The priority document of the present application, French Pat. No. 9901735 filed Feb. 12, 1999 is hereby incorporated by reference.

What is claimed is:

1. A composition for topical use, comprising, in a physiological acceptable medium, from 0.01 to 0.5% by weight relative to the total weight of the composition, one or more oxyethylenated acetylenic diols of formula (I):

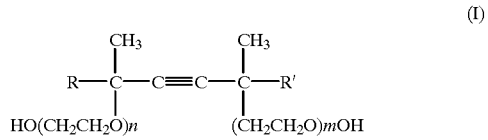

(I)

wherein

R and R' represent, independently of each other, an alkyl radical containing from 1 to 10 carbon atoms;

n and m represent a number ranging from 0 to 10, and the sum n+m is from 2 to 10; and at least one amphiphillic compound having an HLB of 15 or greater.

2. The composition of claim 1, wherein the radicals R and R' in formula (I) are selected from the group consisting of ethyl, methyl, propyl, isopropyl, butyl and isobutyl radical.

3. The composition of claim 1, wherein the diol of formula (I) is a oxyethylenated derivative of 2,4,7,9-tetramethyl-5-decyne-4,7-diol.

4. The composition of claim 1, wherein the oxyethylenated acetylenic diol is in an amount from 0.05 to 0.5% by weight relative to the total weight of the composition.

5. The composition of claim 1, wherein the amphiphillic compound is nonionic.

6. The composition of claim 1, wherein the amphiphillic compound is selected from the group consisting of alkoxylated alkenyl succinates, glycerolated alkenyl succinates, block copolymers of ethylene oxide, block copolymers of propylene oxide, fatty alkyl ethers of a sugar, sorbitan fatty esters, oxyethylenated sorbitan fatty esters, oxyethylenated glycerol esters and mixtures thereof.

7. The composition of claim 1, wherein the amphiphillic compound is in an amount from 0.001 to 10% by weight relative to the total weight of the composition.

8. The composition of claim 1, wherein the weight ratio between the oxyethylenated acetylenic diol and the amphiphillic compound is 1:10 to 10:1.

9. The composition of claim 1, wherein the composition further comprises a fatty phase.

10. The composition of claim 9, wherein the fatty phase is in an amount of 1 to 95% by weight.

11. The composition of claim 1, wherein the composition is a solution, a dispersion, an emulsion or a vesicular dispersion.

12. The composition of claim 1, wherein the composition is a lotion, a gel, a milk or a shampoo.

13. A method of cleansing the skin, mucous membranes, the hair or the eyes comprising, applying the composition of claim 1 to the skin, mucous membrane, hair, or eyes, in need thereof.

14. A method of removing make-up from the skin, mucous membranes, the hair or the eyes comprising, applying the composition of claim 1 to the skin, mucous membrane, hair, or eyes, in need thereof.

15. A process of manufacturing the composition of claim 1, comprising mixing at least one oxyethylenated acetylenic diol of formula (I):

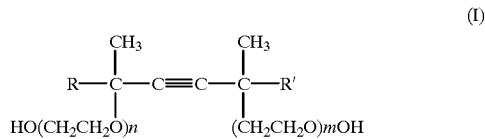

wherein

R and R' represent, independently of each other, an alkyl radical containing from 1 to 10 carbon atoms;

n and m represent a number ranging from 0 to 10, and the sum n+m is from 2 to 10; and at least one amphiphillic compound having an HLB of 15 or greater, in a physiological acceptable medium.

* * * * *